(12) United States Patent
Tepper

(10) Patent No.: US 6,210,330 B1
(45) Date of Patent: Apr. 3, 2001

(54) APPARATUS, SYSTEM AND METHOD FOR REAL-TIME ENDOVAGINAL SONOGRAPHY GUIDANCE OF INTRA-UTERINE, CERVICAL AND TUBAL PROCEDURES

(75) Inventor: Ronnie Tepper, Herzlia (IL)

(73) Assignee: Rontech Medical Ltd., Herzlia (IL)

( * ) Notice: Subject to any disclaimer, the term of this patent is extended or adjusted under 35 U.S.C. 154(b) by 0 days.

(21) Appl. No.: 09/368,175

(22) Filed: Aug. 4, 1999

(51) Int. Cl.[7] ............................................. A61B 8/12
(52) U.S. Cl. ........................... 600/439; 600/463; 600/471
(58) Field of Search .................................. 600/459, 439, 600/463, 471; 606/1, 170–174

(56) References Cited

U.S. PATENT DOCUMENTS

| | | |
|---|---|---|
| 4,671,292 | 6/1987 | Matzuk . |
| 4,681,103 | 7/1987 | Boner et al. . |
| 4,742,829 | 5/1988 | Law et al. . |
| 4,877,033 | 10/1989 | Seitz, Jr. . |
| 4,883,059 | 11/1989 | Stedman et al. . |
| 5,280,427 | 1/1994 | Magnusson et al. . |
| 5,494,039 | * 2/1996 | Onik et al. ............................ 600/461 |
| 5,713,371 | * 2/1998 | Sherman et al. ...................... 600/588 |
| 5,779,626 | * 7/1998 | Kondo .................................. 600/130 |
| 6,066,102 | * 5/2000 | Townsend et al. ................... 600/564 |

FOREIGN PATENT DOCUMENTS

WO99/03399    2/1998    (WO) .

* cited by examiner

*Primary Examiner*—Francis J. Jaworski

(57) ABSTRACT

An apparatus for guidance and monitoring of intra-uterine, cervical and tubal procedures is described, The apparatus includes an assembly, including (a) an endovaginal ultrasound transducer being adapted for insertion into a portion of a patient's vagina so as to be positionable against a cervix of the patient; (b) a cervical holder for holding the cervix; and (c) a connector for interconnecting the ultrasound transducer and the cervical holder, the connector being constructed so as to enable counter resisted movement of the ultrasound transducer relative to the cervical holder, the counter resisted movement being in a direction away from the cervix.

54 Claims, 7 Drawing Sheets

APPARATUS, SYSTEM AND METHOD FOR REAL-TIME ENDOVAGINAL SONOGRAPHY GUIDANCE OF INTRA-UTERINE, CERVICAL AND TUBAL PROCEDURES

FIELD AND BACKGROUND OF THE INVENTION

The present invention relates to apparatus, system and method for real-time endovaginal sonography guidance of intra-uterine, cervical and tubal procedures.

Endovaginal ultrasound transducers for diagnosis and monitoring of obstetric and gynecological disorders are well known in the art.

Examples of endovaginal ultrasound transducers for real-time monitoring and guidance of surgical procedures are disclosed in U.S. Pat. Nos. 4,497,325, 4,671,292, 4,681,103, 4,742,829, 4,877,033, 4,883,059 and 5,280,427, which are incorporated by reference as if fully set forth herein.

Most of these patents provide ultrasound transducers including a needle and/or catheter guide attached thereto for introducing a needle and/or catheter to a targeted tissue. However, the surgical procedures which may be carried out by such endovaginal ultrasound transducers are usually very limited and include puncturing and drainage of abscesses, local tissue sampling and fluid collection. As such, the use of such transducers for real-time monitoring of intra uterine, cervical and tubal procedures is very limited.

Transabdominal ultrasound is not routinely used for real-time monitoring and guidance of such surgical procedures due to its relatively limited resolution, the need to keep the patient's urinary bladder full during operation, and the need of extra-operating stuff.

As a consequence, such surgical procedures are in many cases carried out blindly, relying solely on the "feel" transmitted through manual manipulation of the instrument and the surgeon's experience. However, when the position or size of the uterus is incorrectly diagnosed by the surgeon, uterine perforation may occur. The chances of perforation are higher in the presence of cervical stenosis or uterine malignancy (endometrial or sarcoma).

The main dangers of such uterine perforation include bleeding and trauma to the abdominal viscera as well as damage to internal organs such as bowel, omentum, mesentery, ureter and fallopian tube. Thus, exploration of the abdominal cavity by laparoscopy or laparotomy is often needed due to accidental uterine perforation. Other poor outcomes of blind operation include, for example, failure to completely remove uterine tissues such as placental or fetal tissues, which necessitates a second curettage under general anesthesia, or misplacement of foreign bodies or embryos therein.

Due to the dangers associated with performing non-ultrasound guided procedures, an apparatus for real-time endovaginal sonography guidance of intra-uterine, cervical and tubal surgical and non-surgical procedures has been devised. WO 99/03399 describes an apparatus which includes a cervical holder for holding the patient's cervix and an attached connector for interconnecting an ultrasound transducer to the cervical holder. In contrast to the prior art devices described hereinabove the apparatus described in WO 99/03399 can be used to guide and monitor, in real time, intra uterine, cervical and tubal procedures such as, for example, curettage or evacuation of the uterine cavity for diagnostic and/or therapeutic purposes, and the like.

Although this apparatus provides several advantages over the prior art, which advantages significantly improve the precision with which an intra uterine, cervical and tubal procedures can be performed, several limitations are still inherent to this apparatus.

These limitations arise from the non-compliant nature of this apparatus. As shown in FIG. 1, the apparatus described in WO 99/03399, when in use, is positioned within the vagina and attached via the cervical holder onto cervical tissue, as shown by arrow A. As a result, the ultrasound transducer, connected thereto, contacts a tissue region adjacent to the site of attachment, as shown by arrow B. As such, the site of attachment forms a fulcrum point around which angular movements of the apparatus experienced during the course of a surgical procedure can lead to loss of contact between the ultrasound transducer and the tissue, which loss of contact would result in sub-optimal sonography and a greatly diminished resolution. In addition, movement of the ultrasound transducer in the direction of the tissue region can lead to pressure exerted on the point of attachment which can lead to tissue damage.

There is thus a widely recognized need for, and it would be highly advantageous to have, apparatus, method and system for real-time endovaginal sonography guidance and monitoring of intra-uterine, cervical and tubal surgical and non-surgical procedures devoid of the above limitations.

SUMMARY OF THE INVENTION

According to one aspect of the present invention there is provided an apparatus for guidance and monitoring of intra-uterine, cervical and tubal procedures, the apparatus comprising an assembly, including (a) an endovaginal ultrasound transducer being adapted for insertion into a portion of a patient's vagina so as to be positionable against a cervix of the patient; (b) a cervical holder for holding the cervix; and (c) a connector for interconnecting the ultrasound transducer and the cervical holder, the connector being constructed so as to enable counter resisted movement of the ultrasound transducer relative to the cervical holder, the counter resisted movement being in a direction away from the cervix.

According to another aspect of the present invention there is provided a method of guidance and monitoring of intra-uterine, cervical and tubal procedures, the method comprising the steps of (a) inserting an endovaginal ultrasound transducer into a portion of the patient's vagina, the ultrasound transducer being connected to a cervical holder via a connector, the connector being constructed so as to enable counter resisted movement of the ultrasound transducer relative to the cervical holder, the movement being in a direction away from the cervix of the patient; and (b) fixing the ultrasound transducer against a tissue portion of the patient's cervix via the cervical holder so as to allow for real time monitoring of an intra-uterine, cervical or tubal procedure.

According to yet another aspect of the present invention there is provided a system for guidance and monitoring of a medical instrument utilized in intra-uterine, cervical and tubal procedures, the system comprising (a) an endovaginal ultrasound transducer being adapted for insertion into a portion of a patient's vagina; (b) a cervical holder for holding the patient's cervix; (c) a connector for interconnecting the ultrasound transducer and the cervicholder, the connector being constructed so as to enable counter resisted movement of the ultrasound transducer relative to the cervical holder, the movement being in a direction away from the cervix of the patient; and (d) a device for monitoring an alignment of a medical instrument with respect to an ultrasonic beam produced by the endovaginal ultrasound transducer.

According to still another aspect of the present invention there is provided a method of guiding a medical instrument while monitoring an intra-uterine, cervical or tubal procedures, the method comprising the steps of (a) inserting an endovaginal ultrasound transducer into a portion of the patient's vagina, the ultrasound transducer being connected to a cervical holder via a connector, the connector being constructed so as to enable counter resisted movement of the ultrasound transducer relative to the cervical holder, the movement being in a direction away from the cervix of the patient; (b) fixing the ultrasound transducer against a tissue portion of the patient's vagina or cervix via the cervical holder; (c) inserting a medical instrument through the cervix, aligning the medical instrument with respect to the endovaginal ultrasound transducer and therefore also with respect to an ultrasound beam produced thereby; and (d) monitoring, through the course of the intra-uterine, cervical or tubal procedure, a position of the medical instrument via the ultrasound transducer.

According to further features in preferred embodiments of the invention described below, the connector includes (i) a cervical holder portion being attachable to the cervical holder; and (ii) an ultrasound holder portion being attachable to the cervical holder portion, the ultrasound holder portion including a body and an ultrasound acceptor being for holding the ultrasound transducer, the acceptor is connected to the body of the ultrasound holder portion in a manner so as to allow counter resisted movement of the acceptor relative to the body of the ultrasound holder portion.

According to still further features in the described preferred embodiments the cervical holder includes two arms having a securing member and two holders, the holders being for holding the patient's cervix.

According to still further features in the described preferred embodiments the ultrasound holder portion further includes a spring element interposed between the acceptor and the body such that the counter resisted movement of the acceptor relative to the body in a direction opposite to the patients cervix is counter resisted by the spring element.

According to still further features in the described preferred embodiments the ultrasound holder portion further includes an ultrasound adapter element positioned within the acceptor for firmly holding the ultrasound transducer within the acceptor.

According to still further features in the described preferred embodiments the ultrasound holder portion of the connector is constructed so as to detach from the cervical holder portion upon an application of a force of a predetermined magnitude to the endovaginal ultrasound transducer along a longitudinal axis thereof.

According to still further features in the described preferred embodiments the cervical holder includes an element attached to, or integrally formed with an arm of the two arms, the element being for engaging the cervical holder portion of the connector.

According to still further features in the described preferred embodiments the procedure includes inserting an image transmitting device into the patient's uterine cavity and monitoring the procedure by the image transmitting device.

According to still further features in the described preferred embodiments the image transmitting device is attached to an endoscope.

According to still further features in the described preferred embodiments the image transmitting device includes a CCD.

According to still further features in the described preferred embodiments the image transmitting device includes an optic fiber.

According to still further features in the described preferred embodiments the device includes an extension coaxially connected at a distal end of the endovaginal ultrasound transducer thereby facilitating visual alignment of the medical instrument with respect to the endovaginal ultrasound transducer and therefore also with respect to the ultrasonic beam. Thus, according to still further features in the described preferred embodiments the step of inserting the medical instrument through the cervix, aligning the medical instrument with respect to the endovaginal ultrasound transducer and therefore also with respect to an ultrasound beam produced thereby is effected by a device including an extension coaxially connected at a distal end of the endovaginal ultrasound transducer.

According to still further features in the described preferred embodiments the device includes at least one light beam generator connected either to the connector, to the ultrasound transducer or to the cervical holder, the light beam generator being for generating at least one light beam substantially in a plane defined by the ultrasound beam, the at least one light beam, when impinges on the medical instrument serves for facilitating visual alignment of the medical instrument with respect to the endovaginal ultrasound transducer and therefore also with respect to the ultrasound beam. Thus, according to still further features in the described preferred embodiments the step of inserting the medical instrument through the cervix, aligning the medical instrument with respect to the endovaginal ultrasound transducer and therefore also with respect to an ultrasound beam produced thereby is effected by a device including at least one light beam generator connected either to the connector, to the ultrasound transducer or to the cervical holder, the light beam generator being for generating at least one light beam substantially in a plane defined by the ultrasound beam, the at least one light beam when impinges on the medical instrument serves for facilitating visual alignment of the medical instrument with respect to the endovaginal ultrasound transducer and therefore also with respect to the ultrasound beam.

According to still further features in the described preferred embodiments the device is an imaging device connected to the endovaginal ultrasound transducer, the imaging device being for generating an image of the medical instrument superimposable on a plane defined by the ultrasound beam, thereby facilitating alignment of the medical instrument with respect to the endovaginal ultrasound transducer and therefore also with respect to the ultrasound beam. Thus, according to still further features in the described preferred embodiments the step of inserting the medical instrument through the cervix, aligning the medical instrument with respect to the endovaginal ultrasound transducer and therefore also with respect to an ultrasound beam produced thereby is effected by a device including an imaging device connectable to the endovaginal ultrasound transducer, the imaging device being for generating an image of objects superimposable on a plane defined by the ultrasound beam, thereby facilitating alignment of the medical instrument with respect to the endovaginal ultrasound transducer and therefore also with respect to the ultrasound beam.

According to still further features in the described preferred embodiments the image is displayed on a screen.

According to still further features in the described preferred embodiments the imaging device includes a camera.

According to still further features in the described preferred embodiments the camera is sensitive to light in the visible range.

According to still further features in the described preferred embodiments the camera is an infrared camera.

According to still further features in the described preferred embodiments the imaging device includes an ultrasound generator.

According to still further features in the described preferred embodiments the medical instrument is provided with marks along at least a portion thereof, the marks are identifiable by the imaging device and are therefore usable for image recognition analysis.

According to still further features in the described preferred embodiments the device includes at least two electromagnetic field generators for generating electromagnetic fields, one of the electromagnetic field generator is connected either to the connector, to the ultrasound transducer or to the cervical holder, whereas the other electromagnetic field generator is connected to the medical instrument, the device further includes at least one electromagnetic field sensor of a predetermined position, such that by analyzing magnetic fields perceived by the at least one electromagnetic sensor, spatial information of the relative locations of the electromagnetic field generators and therefore of the endovaginal ultrasound transducer and the medical instrument is obtainable, thereby facilitating alignment of the medical instrument with respect to the ultrasound beam.

According to still further features in the described preferred embodiments the medical instrument is selected from the group consisting of an image transmitting device and a surgical instrument.

The present invention successfully addresses the shortcomings of the presently known configurations by providing a connector for interconnecting an ultrasound transducer and a cervical holder which is constructed so as to enable counter resisted movement in a direction away from the cervix of the ultrasound transducer relative to the cervical holder so as, on one hand, to prevent damage to the cervix and on the other hand to provide superior sonographic images.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
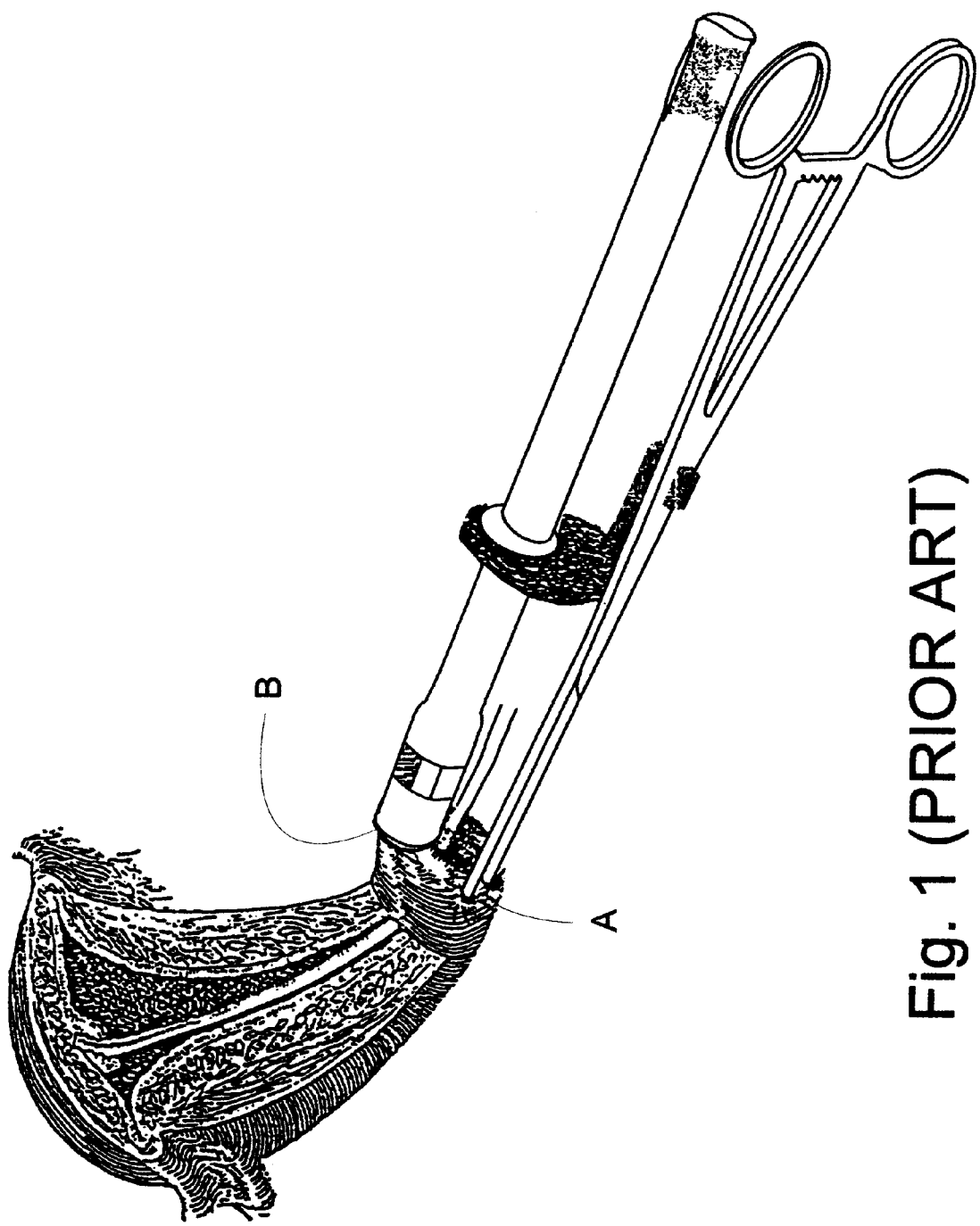
FIG. 1 is an perspective view of a prior art apparatus for guiding and monitoring an intra-uterine procedure illustrating the positioning of such an apparatus relative to a cervix.

The present invention is of an apparatus, method and system which can be used for real-time endovaginal sonography-guidance of intra-uterine, cervical and tubal procedures. Specifically, the present invention can be used to monitor and direct a medical instrument during the course of and intra-uterine, cervical or tubal procedure, which procedure can include, but is not limited to, (i) cureffage or evacuation of the uterine cavity for diagnostic and/or therapeutic purposes; (ii) removal of an endometrial polyp, submucous myoma or other tissue; (iii) introduction or extraction of an intra-uterine contraceptive device (IUCD) and other foreign bodies; (iv) systematic sampling of the endometrium and/or the endocervix for diagnostic purposes; (v) embryo transfer into the endometrial cavity; (vi) embryo transfer into the fallopian tube; (vii) fallopian tube canullation; (viii) ultrasound guided fetal reduction; (ix) simultaneous insertion of an image transmitting device such as endoscopy equipment into the uterine cavity for complementary diagnostic and/or therapeutic purposes; (x) chorionic villi sampling; (xi) fetoscopy; (xii) amniocentesis; (xiii) fetal tissue sampling (xiv) feticid and (xv) hydrosonography with saline or contrast agents.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
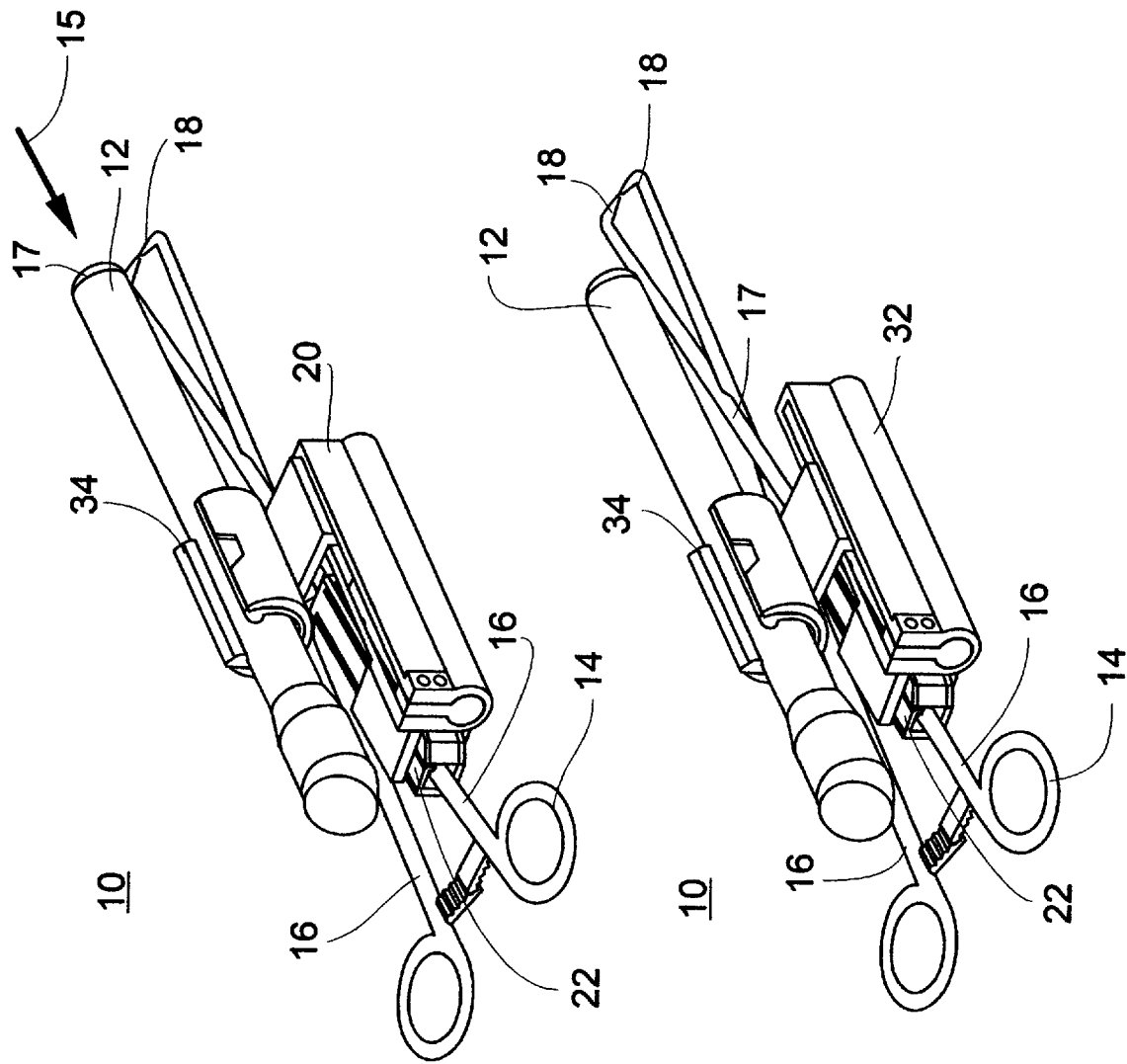
FIGS. 2A and 2B are perspective views of an apparatus for guiding and monitoring an intra-uterine procedure according to the present invention illustrating the direction of movement of the ultrasound transducer relative to a cervical holder.
Figure 3:
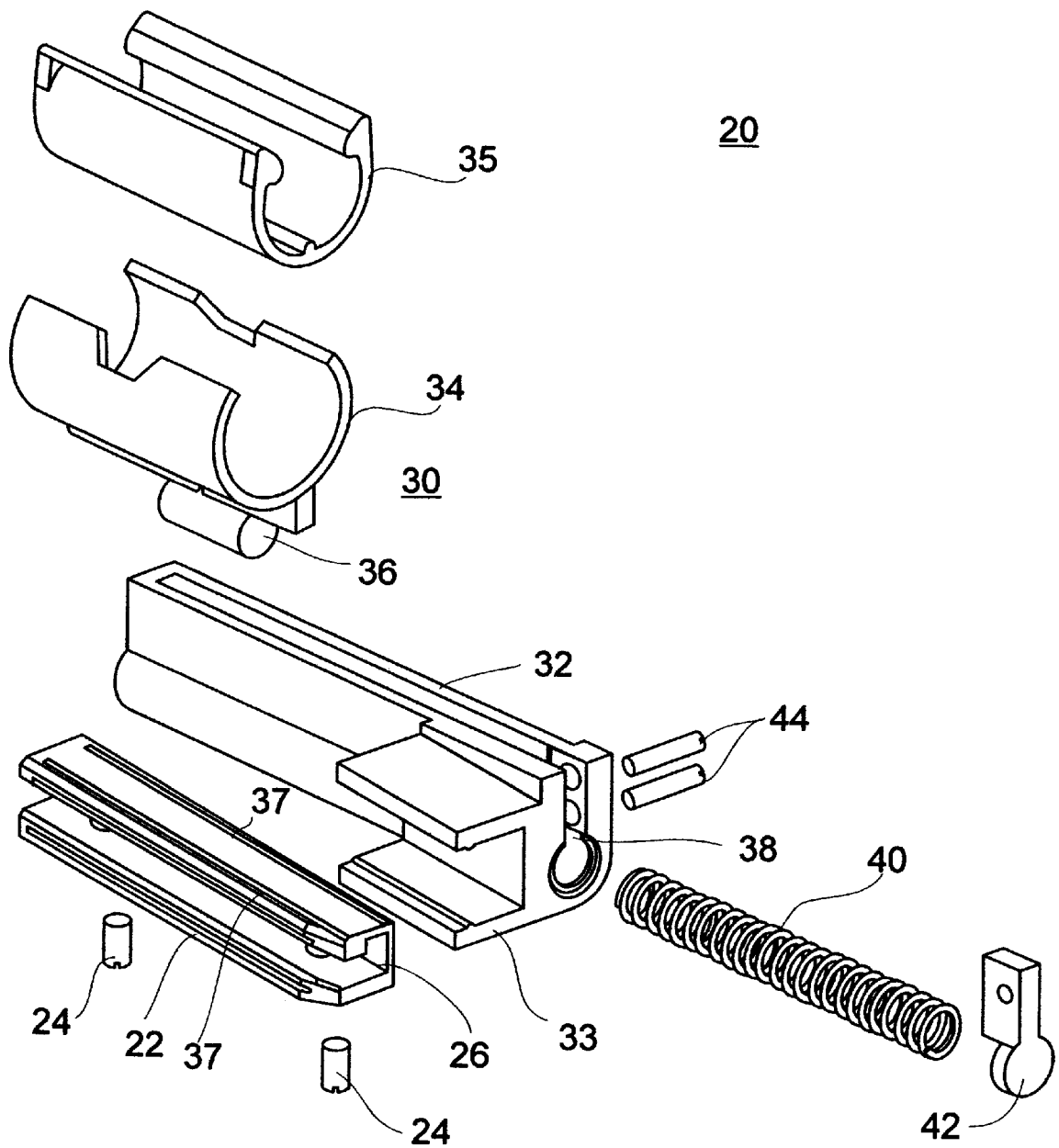
FIG. 3 is an exploded view of cervical and ultrasound holder portions of an apparatus for guiding and monitoring an intra-uterine procedure according to the present invention.

Referring now to the drawings, FIGS. 2A–3 illustrate preferred embodiments of an apparatus according to the present invention, which is referred to hereinbelow as apparatus 10.

Apparatus 10 includes an endovaginal ultrasound transducer 12 adapted for insertion into a portion of a patient's vagina. Ultrasound transducer 12 can be of any type well known in the art, provided that it is constructed such that insertion into a portion of a patient's vagina is enabled. Apparatus 10 further includes a cervical holder 14 for holding a patient's cervix. Cervical holder 14 includes two arms 16 having a securing member 17 and two holders 18. Holders 18 serve for holding the patient's cervix. Cervical holder 14 is typically manually operated and can be any device usable for holding or grasping a tissue. Many examples to such devices are known in the art, and include, but are not limited to clamps, tenaculums and the like. Preferably, cervical holder 14 according to the present invention, is a cervical tenaculum.

Apparatus 10 according to the present invention also includes a connector 20. Connector 20 serves for interconnecting ultrasound transducer 12 and cervical holder 14. As is further detailed hereinbelow, connector 20 is constructed so as to enable counter resisted movement of ultrasound transducer 12 relative to cervical holder 14.

As specifically shown in FIGS. 2A and 2B when a force, as indicated by arrow 15, is applied to a proximal end 17 of ultrasound transducer 12, ultrasound transducer 12 moves in a direction away from the cervix of the patient substantially along a longitudinal axis of apparatus 10. Force 15 is a counter force generated when proximal end 17 of transducer 12 is forced against a cervical or endovaginal tissue region of the patient, when apparatus 10 is in use. As is further detailed hereinbelow, connector 20 is configured such that this movement is counter resisted by a counter force which serves as a returning force. As a result, when apparatus 10 is in use, proximal end 17 of ultrasound transducer 12 maintains contact with a cervical or endovaginal tissue region of the patient. This contact is also maintained when apparatus 10 moves during a procedure as a result of physician manipulation or patient movements.

In sharp contrast, in the prior art apparatus described in WO 99/03399, the ultrasound transducer is immovably fixed to the cervical clamp and as a result, contact between the ultrasound transducer and a cervical tissue region cannot be maintained when this apparatus moves during a procedure.

It will be appreciated that maintaining contact during a procedure is imperative for optimal ultrasound resolution since ultrasound beams require the presence of a water medium, such as biological tissue, to appropriately propagate.

Furthermore, the design described herein with respect to connector 20 provides an additional advantage as is compared with the connector of WO 99/03399. Since holders 18 serve as a fulcrum point, should excess force be applied via end 17 of transducer 12 onto the cervix tissue, transducer 12 is reverse translated so as to reduce the force applied thereby onto the tissue and prevent damage As specifically shown in FIG. 3, and according to a preferred embodiment of the present invention, connector 20 includes a cervical holder portion 22 which is attachable to cervical holder 14. According to one configuration, cervical portion 22 is attached to cervical holder 14 via a groove 26. Groove 26 tightly engages a portion of arm 16 via screws 24 which thread through cervical portion 22 and contact arm 16 of holder. In this configuration, cervical portion 22 is reversibly attachable to cervical holder 14.

Alternatively, cervical portion 22 forms an integral part of holder 14. This is achieved by either manufacturing arm 16 with cervical portion 22, or by permanently attaching cervical portion 22 to arm 16 by gluing, soldering, screwing or any other method for permanent attachment as well known in the art.

Connector 20 also includes an ultrasound holder portion 30 which attaches to cervical holder portion 22. This attachment can be provided by clamping or sliding a U-shaped clasp 33 over grooves 37 provided on cervical holder portion 22. Holder portion 30 of connector 20 is preferably constructed so as to enable the detachment of ultrasound transducer 12 from cervical holder portion 22 upon an application of a force of a predetermined magnitude to proximal end 17 of ultrasound transducer 12 along a longitudinal axis thereof. For example, if force 15 applied to proximal end 17 of transducer 12 exceeds a predetermined magnitude, above which tissue damage can occur at the site of contact between transducer 12 and a cervical or endovaginal tissue region, the connection between cervical clamp 14 and transducer 12 disintegrates. This feature of apparatus 10 of the present invention also prevents damage to cervical tissue held by holders 18 of cervical holder 14, since excessive force in the direction of the cervix can lead to an excessive pulling force on the adjacent tissue by cervical holder 14.

Ultrasound holder portion 30 includes a body 32 and an ultrasound acceptor 34 which serves for holding ultrasound transducer 12.

According to a preferred embodiment of the present invention, ultrasound holder portion 30 further includes an ultrasound adapter element 35 positioned within acceptor 34 for firmly holding ultrasound transducer 12 within acceptor 34. It will be appreciated that adapter element 35 can be configured in a variety of sizes and shapes so as to accommodate a variety of ultrasound transducers 12 having different sizes.

As is mentioned hereinabove, connector 20 is constructed so as to enable counter resisted movement of ultrasound transducer 12 relative to cervical holder 14.

Thus, according to a preferred embodiment of the present invention, acceptor 34 is connected to body 32 in a manner so as to allow counter resisted movement of acceptor 34 relative to body 32 along a longitudinal axis of apparatus 10. This is achieved by providing acceptor 34 with a tongue element 36, which fits within a slot 38 formed in body 32. This configuration allows movement of acceptor 34 relative to body 32 along a longitudinal axis of body 32 and therefore along a longitudinal axis of apparatus 10. To counter resist this movement, ultrasound holder portion 30 is provided with a spring element 40 positioned within slot 38. Spring element 40 is retained within slot 38 via a stoppage 42 and pins 44. Thus, movement of acceptor 34 in a direction away from the cervix of a patient, when apparatus 10 is utilized, is counter resisted by spring element 40. Although spring element 40 is depicted in FIG. 3 as a coil spring, any element with elastic properties can be utilized by apparatus 10 of the present invention, examples include, but not limited to elastomers.

It will be appreciated that the above described configuration is one configuration of apparatus 10 with which counter resisted movement of ultrasound transducer 12 relative to cervical holder 14 can be realized. Alternative configurations employing spring elements at a point of attachment between ultrasound holder portion 30 and cervical holder portion 22, or alternatively between cervical holder portion 22 and arm 16 of holder 14 can also be realized and utilized by apparatus 10 of the present invention.

It will be appreciated that ultrasound holder portion 30 and the detachable embodiment of cervical holder portion 22 can be manufactured from a variety of materials such as, but not limited to, plastics, metals and composite materials. Portions 30 and 22 can be fabricated via injection molding, CNC and the like and can be either disposable or reusable in which case portions 30 and 22 are fabricated out of autoclavable materials.

According to another aspect of the present invention, apparatus 10 is utilized to monitor a variety of intra-uterine, cervical or tubal procedures.

Thus, monitoring of such procedures is effected by the following method steps in which, in a first step, apparatus 10 is assembled by connecting ultrasound holder portion 30 to element 22 which is attached to, or integrally formed with, cervical holder 14. Following this step, ultrasound transducer 12 is attached to acceptor 34 via adapter 35, and it is appropriately positioned. Apparatus 10 is then inserted into the patients vaginal cavity and ultrasound transducer 12 is positioned against the patient's endovaginal or cervical tissue region and cervical holder 14 is then used to grip an adjacent cervical or endovaginal tissue region of a patient by means of holders 18. Alternatively holder portions 30 and 22 are assembled, inserted and positioned within the vagina of a patient via cervical holder 14, following which ultrasound transducer 12 is attached to holder 30 and is appropriately positioned.

During an intra-uterine procedure, apparatus 10 is preferably held by one hand of the physician via cervical holder 14, so that the other hand is free to conduct the procedure. Since the diameter of ultrasound transducer 10 is substantially small, the physician may conveniently introduce a medical instrument through the cervix of the patient into the uterine cavity. The surgical procedure is then carried out and is continuously guided and monitored by means of ultrasound transducer 12.

It will be appreciated by one ordinarily skilled in the art that guiding a medical instrument is used herein as a non limiting example for guiding any medical instrument (tool) for diagnostic and/or surgical purposes into the cervix, uterine or fallopian tubes of the patient. Such instruments include, but are not limited to, uterine sound—plastic disposable or stainless steel, uterine dilators—hegar double or single end, uterine curettes, uterine dressing, hysterectomy forceps, ovum forceps, intra-uterine device remover, biopsy punches, endocervical speculum, aspirate cureffe, vacuum curette, aspirate tube, coagulator, embryo transfer set, insemination device, embryo gamete intra-fallopian transfer (GIFT) catheter, embryo intra uterine insemination (IUI) catheter, Karman catheter for uterine aspiration, minimally invasive surgery equipment, such as, grasping forceps, scissors, light dissecting/grasping forceps, diathermy balloon intra cavitary, IUCD, hysterosalpingography catheter, uterine catheter, tubal catheter, brush cytology, cervical adapter for hydrotubation, uterine controlling instruments, vacuum intra-uterine sound, uterine elevator, Spackmann cannula, Scott uterine manipulator, Hulka controlling tenaculum or forceps, rocket vacuum aspirator curette, uterine depth probe, sampling devices, NOVAK, KEVORKIAN, EXPORA and Pipelle.

It will be appreciated that since the above listed medical instruments are typically operated by the strong (i.e., skilled) hand of the physician, apparatus 10 is held and operated by the weak hand thereof. As such, apparatus 10 is preferably constructed of a light material such that it can be easily held in place and maneuvered by the physician.

According to another aspect of the present invention apparatus 10 is used in combination with an image transmitting device included within a system for guidance and monitoring of a medical instrument utilized in intra-uterine, cervical and tubal procedures.

The image transmitting device may be, for example, an optic fiber, or endoscopy equipment. The image transmitting device may include an image transmitting element such as a CCD or a video camera. The image transmitting device is preferably connected to apparatus 10, such that ultrasound transducer 12 is preferably inserted into the patient's vagina and the image transmitting device is preferably inserted through the cervical canal into the uterine cavity.

For example, transducer 12 may be connected to an endoscopy equipment so as to allow simultaneous monitoring of the surgical procedure by means of two complementary methods, thereby enabling to accurately determine the position of a medical instrument with relation to the uterine wall.

The system described hereinabove not only allows for ultrasonic view of the treated area in the cervix, uterine or fallopian tube, it further allows for ultrasonic view of the operating medical instrument. This can be effected by this system provided that the medical instrument is brought "inside" or "into" the beam generated by the ultrasound transducer, which beam is shaped as a triangle located within the ultrasound plane of view.

Since apparatus 10 is inserted into a portion of the vagina of the patient prior to the insertion of a medical instrument through the cervix, and further since the medical instrument and apparatus 10 are each held by a different hand of the surgeon, an unskilled physician may find it difficult to bring the medical instrument "inside" or "into" the sonography beam.

As further detailed hereinunder, the following embodiments the present invention specifically address this problem.

With reference now to FIGS. 4–7, presented is a system for guidance and monitoring of intra-uterine, cervical and tubal procedures, which is referred to hereinbelow as system 50.

System 50 includes apparatus 10 for generating an ultrasound beam from ultrasound transducer 12 included within apparatus 10 as further described hereinabove with respect to FIGS. 2A and 2B.

System 50 further includes a medical instrument 60. Instrument 60 serves to perform the intra-uterine, cervical or tubal procedure and is typically operable by a strong hand of the surgeon. Medical instrument 60 may be a diagnostic instrument, such as, but not limited to, hysterosalpingography catheter, uterine catheter, tubal catheter, brush cytology, cervical adapter for hydrotubation, uterine controlling instruments, vacuum intra-uterine sound, uterine elevator, Spackmann cannula, Scott uterine manipulator, Hulka controlling tenaculum or forceps, rocket vacuum aspirator curette, uterine depth probe, sampling devices, NOVAK, KEVORKIAN, EXPORA and Pipelle, or a surgical instrument, such as, but not limited to, uterine sound—plastic disposable or stainless steel, uterine dilators—hegar double or single end, uterine curettes, uterine dressing, hysterectomy forceps, ovum forceps, intra-uterine device remover, biopsy punches, endocervical speculum, aspirate cureffe, vacuum cureffe, aspirate tube, coagulator, embryo transfer set, insemination device, embryo gamete intra-fallopian transfer (GIFT) catheter, embryo intra uterine insemination (IUI) catheter, Karman catheter for uterine aspiration, minimally invasive surgery equipment, such as, grasping forceps, scissors, light dissecting/grasping forceps, diathermy balloon intra cavitary and IUCD.

System 50 further includes a device 62 which serves for monitoring the alignment of medical instrument 60 with respect to ultrasound transducer 12 and therefore also with respect to the ultrasound beam generated thereby.

Several exemplary embodiments of device 62 are described hereinbelow. Each of which readily enables the surgeon to align the medical instrument employed with the ultrasound transducer and therefore also with the beam generated thereby. By inserting the medical instrument coaxially with its alignment, the surgeon ensures that the medical instrument is moved on the plane in which the ultrasound beam resides and therefore, eventually the instrument will be visualized in the ultrasound image obtained. This procedure assists the surgeon in bringing the medical instrument "inside" or "into" the ultrasound beam. Device 62 is typically connected to the distal end of transducer 12 via a suitable connector, generally marked as 64. However, direct connection, and connection to other locations on apparatus 10 are also envisaged.

Connector 64 is preferably equipped with wings 65, being aligned within the plane of the ultrasound beam. To this end, distal end 68 of transducer 12, is asymmetrically formed, such that when connector 64 is applied thereon, wings 65 acquire their respective positions.

Figure 4:
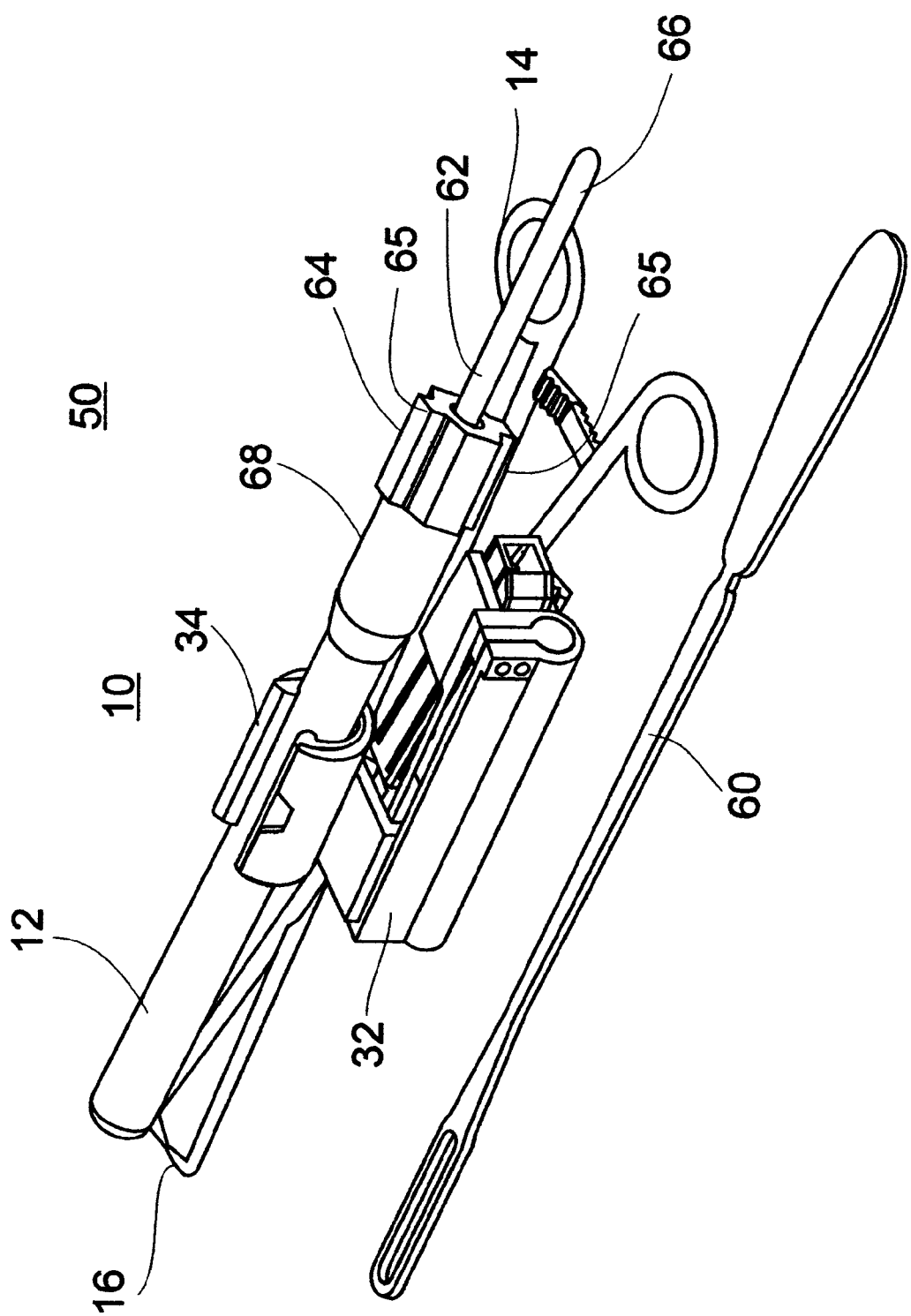
FIGS. 4–7 are schematic illustrations of alternative embodiments of a system according to the present invention including the apparatus shown in FIG. 2, a medical instrument and a device for monitoring the alignment of the medical instrument with respect to the ultrasound transducer and therefore also with respect to the ultrasound beam.

As specifically shown in FIG. 4, and according to one embodiment, device 62 includes an extension 66 coaxially connected at a distal end 68 of ultrasound transducer 12, thereby facilitating visual alignment of medical instrument 60 with respect to ultrasound transducer 12 and therefore also with respect to the ultrasound beam generated thereby.

According to this embodiment, while inserting medical instrument 60 through the cervix of the patient, the surgeon ensures that instrument 60 is positioned parallel to extension 66, to thereby direct instrument 60 "inside" or "into" the ultrasound beam.

Figure 5:
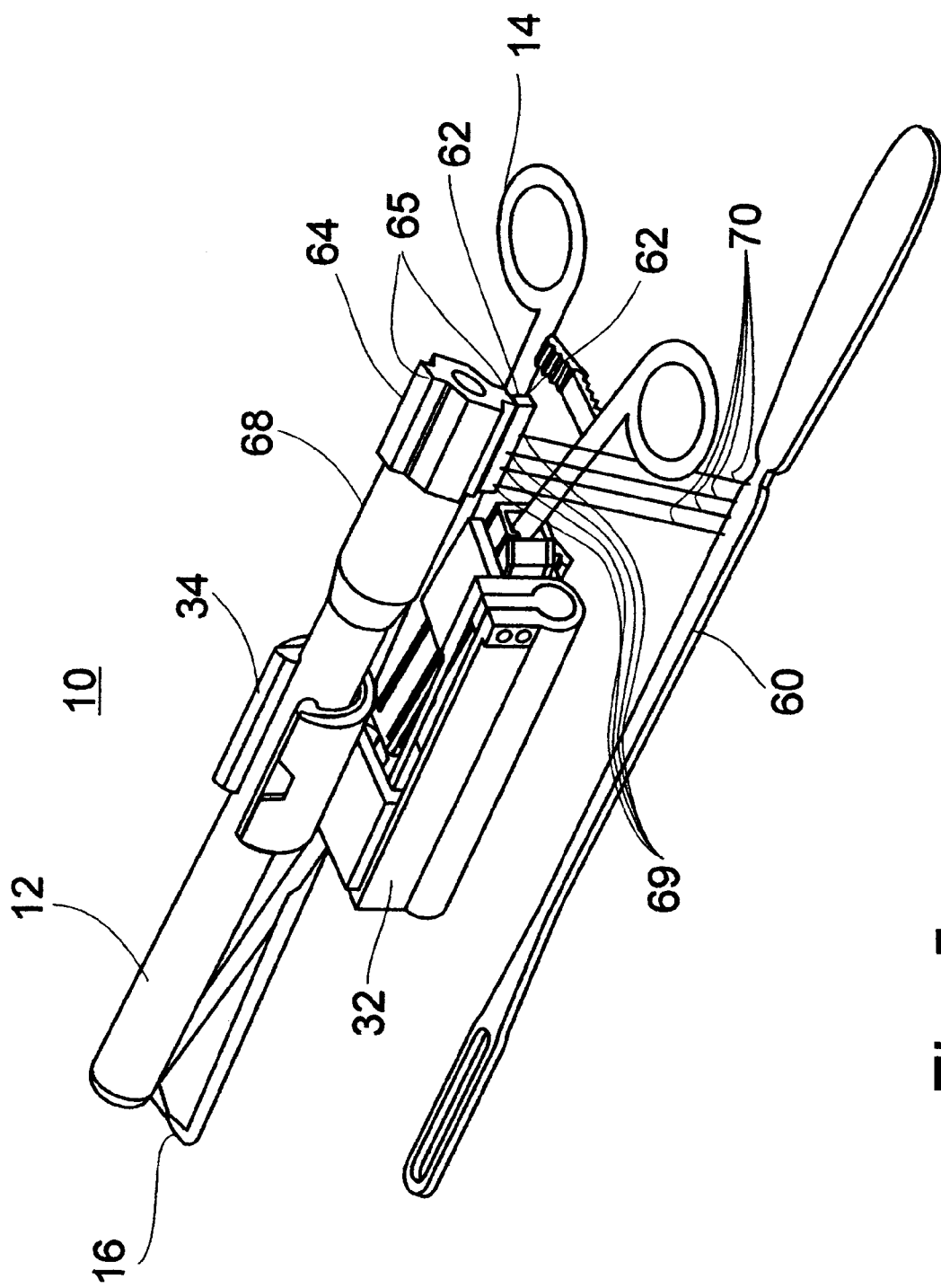

As specifically shown in FIG. 5, and according to yet another embodiment of the present invention, device 62 includes at least one light beam generator 69 (four are shown) connected to apparatus 10, preferably to transducer 12 thereof, preferably via connector 64. Light beam generators 69 serve for generating at least one focused light beam 70. Light beams 70 are projected perpendicular to the plane defined by the ultrasound beam of transducer 12.

Light beams 70 impinging on medical instrument 60, serve for facilitating visual alignment of medical instrument with respect to endovaginal ultrasound transducer 12 and therefore also with respect to the ultrasound beam.

Each of light beam generators 68 may be, for example, a laser source, generating, for example, a green laser beam, which is known not to be absorbed by living tissues. However, non-coherent light sources are also applicable.

According to this embodiment of the invention, while inserting medical instrument 60 through the cervix of the patient, the surgeon ensures that light beams 70 impinge on instrument 60, to thereby direct instrument 60 "inside" or "into" the ultrasound beam of transducer 12. Light beam generators 68 preferably receive energy from a power source, e.g., a battery, implemented in a battery housing located within connector 64.

Each of generators 68 may be, for example, a pointer type laser diode, having, for example, a maximum output below 5 mW, wavelength of 650 nm, with beam dimensions of about 3.0 nm×2.5 nm. A suitable diode is the "ES smallest laser pointer" Cat. No. D53,050 which is available from Edmund Scientific, Industrial Optics Division, Barrington, N.J. 08007-1380 U.S.A. Generators 68 may alternatively be selected to generate a stripe of light. Edmund Scientific Cat. No. D52,562 "Gammax-xlaser light show".

Each of generators 68 preferably further includes a beam splitter, e.g., a TECH SPEC pellicle beam splitter. The pellicles are very thin nitrocellulose membranes bonded to lapped aluminum frames. Ghost images are eliminated by the thinness of the membrane as the second surface reflection superimposed on the first surface reflection. The uncoated pellicle reflects 8% and transmits 92% through the visible and near infrared regions. The pellicles' thickness is in the range of 2 μm, their index of reflection is (Nd):1.5. Suitable pellicles are available from Edmund Scientific, Industrial Optics Division, Barrington, N.J. 08007-1380 U.S.A., Cat. No. D39,478).

Figure 6:
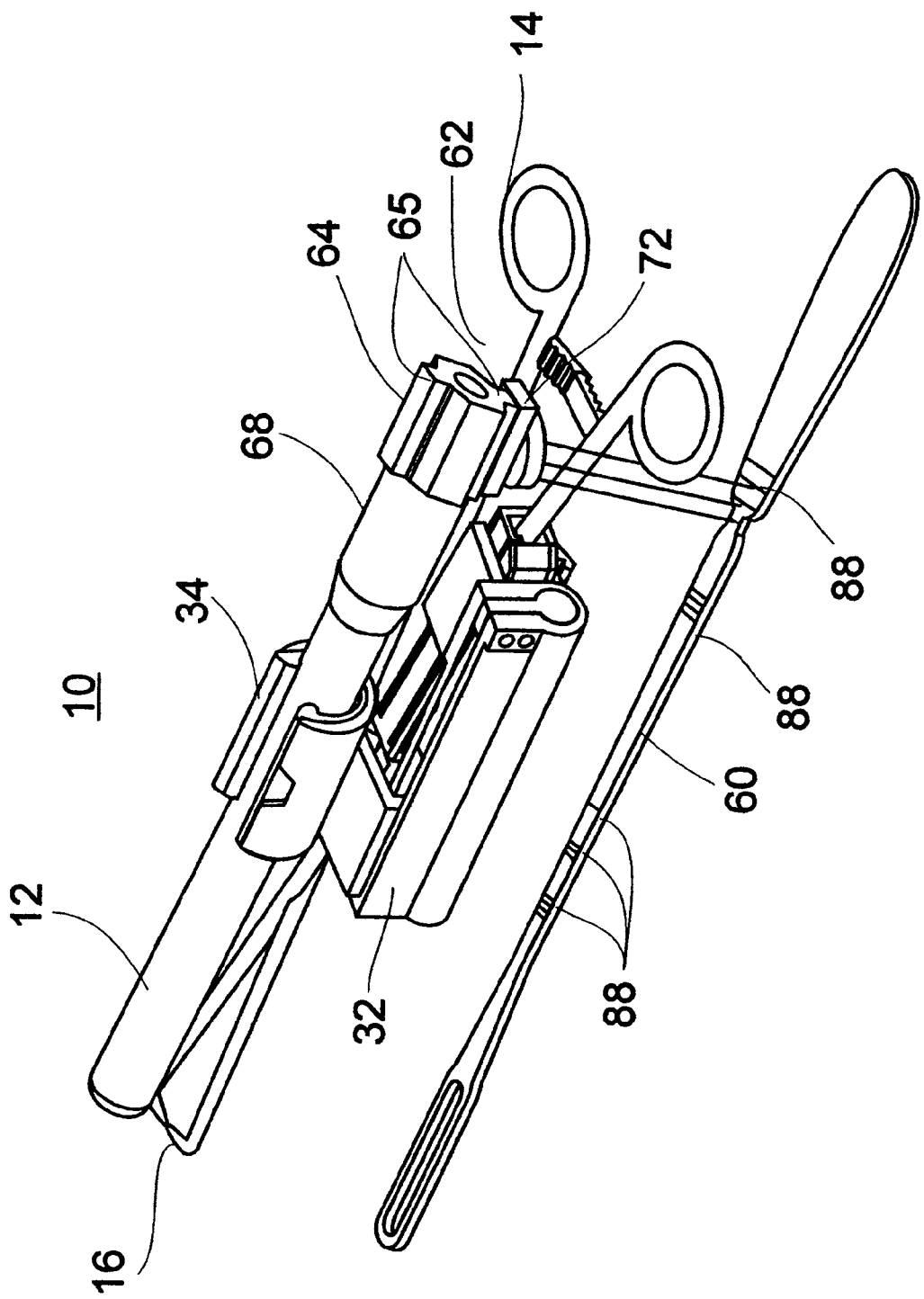

As specifically shown in FIG. 6, and according to still another embodiment of the present invention, device 62 includes an imaging implement 72 connected to apparatus 10, preferably to transducer 12 thereof, preferably via connector 64. Imaging implement 72 serves for generating an image of objects in the plane defined by the ultrasound beam. Implement 72 thereby serves for facilitating alignment of medical instrument 60 with respect to endovaginal ultrasound transducer 12 and therefore also with respect to the ultrasound beam generated thereby. According to this embodiment, while inserting medical instrument 60 through the cervix of the patient, the surgeon ensures that imaging implement 72 "sees" or "captures" instrument 60, to thereby direct instrument 60 "inside" or "into" the ultrasound beam. The image generated by implement 72 is preferably displayed on a screen. A single screen may serve for presenting, in real time, the image perceived through imaging implement 72 superimposed on top of the ultrasound image perceived through transducer 12 such that a relative positioning can be assessed and used to guide medical instrument 60 accordingly.

Implement 72 is positioned such that when an image showing instrument 60 in, for example, a vertical alignment with respect to the screen then the surgeon knows that medical instrument 60 is aligned with respect to endovaginal ultrasound transducer 12 and therefore also with respect to the ultrasound beam generated thereby. The screen may further provide a displayed grid or coordinates, such that assessment of the verticality of the image of instrument 60 is facilitated. Implement 72 preferably receive energy from a power source, e.g., a battery, implemented in a battery housing located within connector 64.

According to a preferred embodiment of the present invention imaging implement 72 is a camera, e.g., a charge coupled device (CCD) camera equipped with a lens or optic fibers arrangement, which is adapted to perceive light in the visible range. According to an alternative embodiment of the present invention implement 72 is a camera sensitive to light in the infrared range, i.e., an infrared (thermal) camera, which may similarly include a lens or an optic fibers arrangement. According to yet another preferred embodiment of the invention imaging implement 72 is an ultrasound implement. According to yet another preferred embodiment of the present invention imaging implement 72 is an X ray implement. In the latter case, an X rays sensitive plate is provided to perceive the image of instrument 60 thereby. Such plates are well known in the art.

According to each of the imaging embodiments described herein an image of instrument 60 is generated, which image enables the surgeon to direct instrument 60 "inside" or "into" the beam generated by ultrasound transducer 12.

As further shown in FIG. 6, according to a preferred embodiment of the present invention medical instrument 60 is provided with marks 88 along at least a portion thereof. Marks 88 are selected identifiable by imaging implement 72 of choice and are therefore usable for image recognition analysis, which may be used to estimate the depth to which instrument 60 has been inserted at any given time. Image recognition is well known art and therefore will not be further elaborated upon herein.

The nature of marks 88 must depend on the nature of imaging implement 72 of choice. Thus, if a CCD camera is selected, marks 88 may acquire a color distinguishable from the background color of instrument 60. If an infrared (thermal) camera is selected, marks 88 may be applied, for example, as substances of increased or decreased heat conductivity as compared with the substance from which instrument 60 is made. If ultrasound or X ray implements are selected, marks 88 may be applied, for example, as holes, recessions, protrusions, etc., to render them distinguishable from the background of instrument 60. In each of these cases, marks 88 may be further selected distinguishable from one another in a fashion, e.g., similar to a bar-code, such that image recognition analysis may be applied.

A suitable CCD is a CCD sensitive to light at 0.2 lux, having a S/N ratio greater than 46 dB. The CCD is preferably monochromatic and is capable of sensing an area of 6.4×4.8 mm. The CCD preferably features miniature size e.g., 30×30×60 mm, and low weight, e.g., 120 grams. A CCD corresponding to the above criteria is distributed by Edmund Scientific, Cat No. D39,244.

Figure 7:
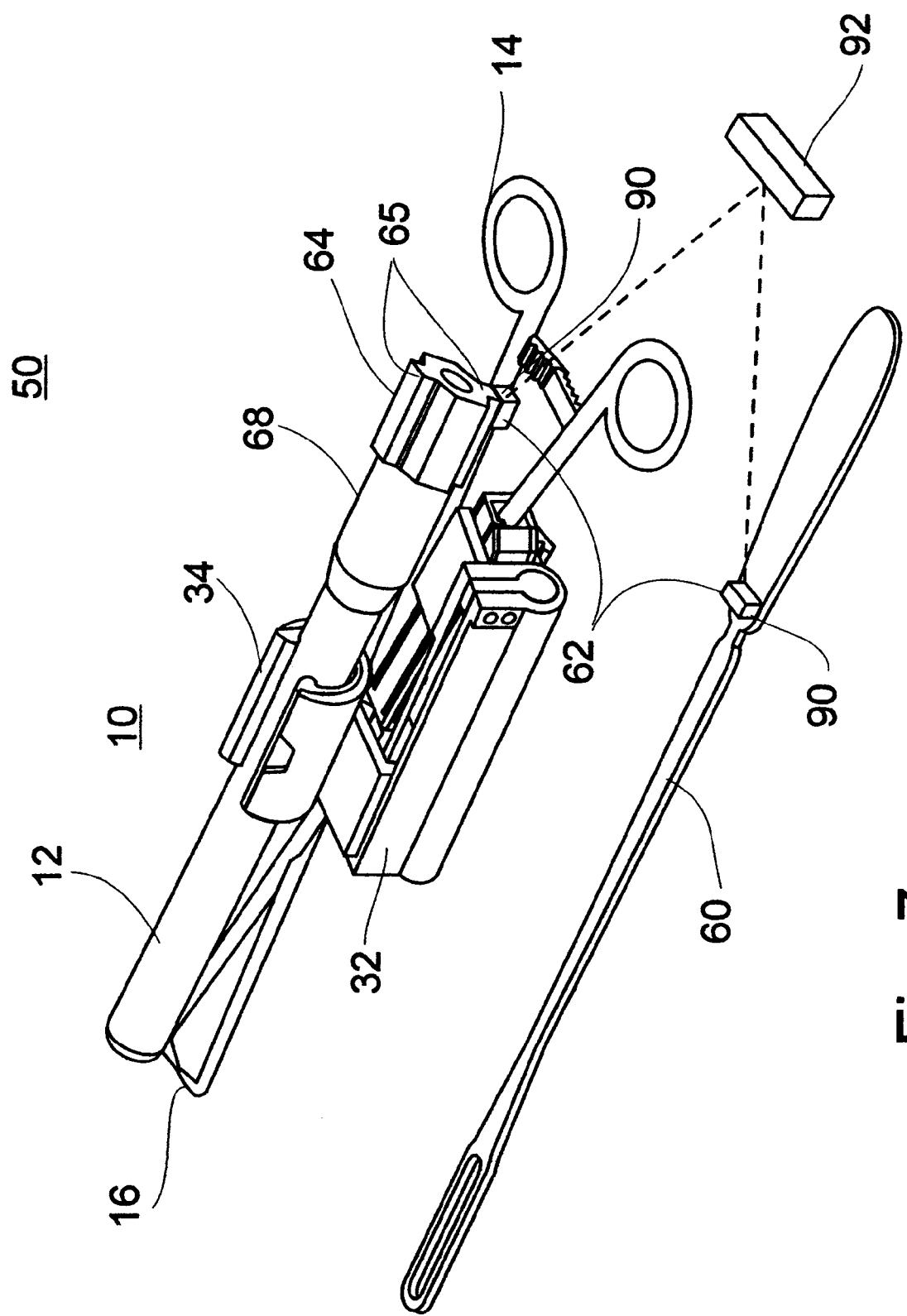

As specifically shown in FIG. 7, according to still another embodiment of the present invention device 62 includes at least two electromagnetic field generators 90 which serve for generating electromagnetic fields. One of electromagnetic field generators 90 is connected to apparatus 10, preferably to transducer 12 thereof, preferably via connector 64. The other electromagnetic field generator 90 is connected to medical instrument 60. According to this embodiment of the present invention, device 62 further includes at least one electromagnetic field sensor, generally indicated by 92. Sensor 92 is positioned in a predetermined position outside the patients body, such that by analyzing the magnetic fields perceived by sensor 92, spatial information of the relative locations of electromagnetic field generators 90 and therefore of transducer 12 and medical instrument 60 is obtainable, thereby facilitating alignment of medical instrument 60 with respect to endovaginal ultrasound transducer 12 and therefore also with respect to the ultrasound beam generated thereby. Further description concerning the operation of electromagnetic field generators and electromagnetic field sensors and the use of sensors to retrieve spatial information from generators is disclosed in, for example, PCT/IL96/00050 (WO 97/03609) and further in U.S. Pat. No. 4,945,305, both are incorporated by reference as if fully set forth herein. Generators 90 are preferably powered by a mutual power source implemented in a dedicated housing in connector 64 or by independent power sources. Suitable power wiring is envisaged.

Further according to the present invention there is provided a method of guiding a medical instrument while monitoring an intra-uterine, cervical or tubal procedures. The method is effected by the following method steps in which in a first step ultrasound transducer 12, mounted within apparatus 10 of system 50 is inserted into a portion of the patient's vagina and ultrasound transducer 12 is fixed against a tissue portion of the patient's vagina or cervix via cervical holder 14. Alternatively, holder portions 30 and 22 of apparatus 10 are inserted and positioned within the vagina of a patient via cervical holder 14, following which ultrasound transducer 12 is attached holder 30 and appropriately positioned.

In a second step of the method according to the present invention, a medical instrument 60 is inserted through the cervix and aligned with respect to ultrasound transducer 12 and therefore also with respect to an ultrasound beam produced thereby. Thus, system 50 according to the present invention allows to monitor through the course of the intra-uterine, cervical or tubal procedure, a position of medical instrument 60.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An apparatus for guidance and monitoring of intra-uterine, cervical and tubal procedures, the apparatus comprising an assembly, including:
    (a) an endovaginal ultrasound transducer being adapted for insertion into a portion of a patient's vagina so as to be positionable against a cervix of the patient;
    (b) a cervical holder for holding the cervix; and
    (c) a connector for interconnecting said ultrasound transducer and said cervical holder, said connector being constructed so as to enable counter resisted movement of said ultrasound transducer relative to said cervical holder, said counter resisted movement being in a direction away from the cervix.

2. The apparatus of claim 1, wherein said connector includes:
    (i) a cervical holder portion being attachable to said cervical holder; and
    (ii) an ultrasound holder portion being attachable to said cervical holder portion, said ultrasound holder portion including a body and an ultrasound acceptor being for holding said ultrasound transducer, said acceptor is connected to said body of said ultrasound holder portion in a manner so as to allow counter resisted movement of said acceptor relative to said body of said ultrasound holder portion.

3. The apparatus of claim 2, wherein said ultrasound holder portion further includes a spring element interposed between said acceptor and said body such that said counter resisted movement of said acceptor relative to said body in a direction opposite to the patients cervix is counter resisted by said spring element.

4. The apparatus of claim 2, wherein said ultrasound holder portion further includes an ultrasound adapter element positioned within said acceptor for firmly holding said ultrasound transducer within said acceptor.

5. The apparatus of claim 2, wherein said ultrasound holder portion of said connector is constructed so as to detach from said cervical holder portion upon an application of a force of a predetermined magnitude to said endovaginal ultrasound transducer along a longitudinal axis thereof.

6. The apparatus of claim 1, wherein said cervical holder includes two arms having a securing member and two holders, said holders being for holding the patient's cervix.

7. The apparatus of claim 6, wherein said cervical holder includes an element attached to, or integrally formed with an arm of said two arms, said element being for engaging said cervical holder portion of said connector.

8. A method of guidance and monitoring of intra-uterine, cervical and tubal procedures, the method comprising the steps of:
    (a) inserting an endovaginal ultrasound transducer into a portion of the patent's vagina, said ultrasound transducer being connected to a cervical holder via a connector, said connector being constructed so as to enable counter resisted movement of said ultrasound transducer relative to said cervical holder, said movement being in a direction away from the cervix of the patient; and
    (b) fixing said ultrasound transducer against a tissue portion of the patient's cervix via said cervical holder so as to allow for real time monitoring of an intra-uterine, cervical or tubal procedure.

9. The method of claim 8, further comprising providing said connector with:
    (i) a cervical holder portion and attaching said cervical holder portion to said cervical holder; and
    (ii) an ultrasound holder portion and attaching said ultrasound holder portion to said cervical holder portion, said ultrasound holder portion including a body and an ultrasound acceptor being for holding said ultrasound transducer, said acceptor being connected to said body in a manner so as to allow counter resisted movement of said acceptor relative to said body along a longitudinal axis of the apparatus.

10. The method of claim 9, further comprising providing said ultrasound holder portion with a spring element interposed between said acceptor and said body such that said counter resisted movement of said acceptor relative to said body in a direction opposite to the patients cervix is counter resisted by said spring element.

11. The method of claim 9, further comprising providing said ultrasound holder portion with an ultrasound adapter element positioned within said acceptor for firmly holding said ultrasound transducer within said acceptor.

12. The method of claim 9, further comprising providing said ultrasound holder portion of said connector with a construction so as to detach from said cervical holder portion upon an application of a force of a predetermined magnitude to said endovaginal ultrasound transducer along a longitudinal axis thereof.

13. The method of claim 8, further comprising providing said cervical holder with two arms having a securing member, and two holders, said holders being for holding the patient's cervix.

14. The method of claim 13, further comprising providing said cervical holder with an element attached to, or integrally formed with an arm of said two arms, said element being for engaging said cervical holder portion of said connector.

15. The method of claim 8, wherein said procedure includes inserting as image transmitting device into the patient's uterine cavity and monitoring the procedure by said image transmitting device.

16. The method of claim 15, further comprising providing said image transmitting device attached to an endoscope.

17. The method of claim 15, further comprising providing said image transmitting device with a CCD.

18. The method of claim 15, further comprising providing said image transmitting device with an optic fiber.

19. A system for guidance and monitoring of a medical instrument utilized in intra-uterine, cervical and tubal procedures, the system comprising:
    (a) an endovaginal ultrasound transducer being adapted for insertion into a portion of a patient's vagina;
    (b) a cervical holder for holding the patient's cervix;
    (c) a connector for interconnecting said ultrasound transducer and said cervicholder, said connector being constructed so as to enable counter resisted movement of said ultrasound transducer relative to said cervical holder, said movement being in a direction away from the cervix of the patient; and
    (d) a device for monitoring an alignment of a medical instrument with respect to an ultrasonic beam produced by said endovaginal ultrasound transducer.

20. The system of claim 19, wherein said connector includes:
    (i) a cervical holder portion being attachable to said cervical holder; and
    (ii) an ultrasound holder portion being attachable to said cervical holder portion, said ultrasound holder portion including a body and an ultrasound acceptor being for holding said ultrasound transducer, said acceptor is connected to said body in a manner so as to allow counter resisted movement of said acceptor relative to said body along a longitudinal axis of the apparatus.

21. The system of claim 20, wherein said ultrasound holder portion further includes a spring element interposed between said acceptor and said body such that said counter resisted movement of said acceptor relative to said body in a direction opposite to the patients cervix is counter resisted by said spring element.

22. The system of claim 20, wherein said ultrasound holder portion further includes an ultrasound adapter element positioned within said acceptor for firmly holding said ultrasound transducer within said acceptor.

23. The system of claim 20, wherein said ultrasound holder portion of said connector is constructed so as to detach from said cervical holder portion upon an application of a force of a predetermined magnitude to said endovaginal ultrasound transducer along a longitudinal axis thereof.

24. The system of claim 19, wherein said cervical holder includes two arms having a securing member, and two holders, said holders being for holding the patient's cervix.

25. The system of claim 24, wherein said cervical holder includes an element attached to, or integrally formed with an arm of said two arms, said element being for engaging said cervical holder portion of said connector.

26. The system of claim 19, wherein said device includes an extension coaxially connected at a distal end of said endovaginal ultrasound transducer thereby facilitating visual alignment of said medical instrument with respect to said endovaginal ultrasound transducer and therefore also with respect to said ultrasonic beam.

27. The system of claim 19, wherein said device includes at least one light beam generator connected either to said connector, to said ultrasound transducer or to said cervical holder, said light beam generator being for generating at least one light beam substantially in a plane defined by said ultrasound beam, said at least one light beam, when impinges on said medical instrument serves for facilitating visual alignment of said medical instrument with respect to said endovaginal ultrasound transducer and therefore also with respect to said ultrasound beam.

28. The system of claim 19, wherein said device is an imaging device connected to said endovaginal ultrasound transducer, said imaging device being for generating an image of said medical instrument superimposable on a plane defined by said ultrasound beam, thereby facilitating alignment of said medical instrument with respect to said endovaginal ultrasound transducer and therefore also with respect to said ultrasound beam.

29. The system of claim 28, wherein said image is displayed on a screen.

30. The system of claim 28, wherein said imaging device includes a camera.

31. The system of claim 30, wherein said camera is sensitive to light in the visible range.

32. The system of claim 30, wherein said camera is an infrared camera.

33. The system of claim 28, wherein said imaging device includes an ultrasound generator.

34. The system of claim 28, wherein said medical instrument is provided with marks along at least a portion thereof, said marks are identifiable by said imaging device and are therefore usable for image recognition analysis.

35. The system of claim 19, wherein said device includes at least two electromagnetic field generators for generating electromagnetic fields, one of said electromagnetic field generator is connected either to said connector, to said ultrasound transducer or to said cervical holder, whereas the other electromagnetic field generator is connected to said medical instrument, the device further includes at least one electromagnetic field sensor of a predetermined position, such that by analyzing magnetic fields perceived by said at least one electromagnetic sensor, spatial information of the relative locations of said electromagnetic field generators and therefore of said endovaginal ultrasound transducer and said medical instrument is obtainable, thereby facilitating alignment of said medical instrument with respect to said ultrasound beam.

36. The system of claim 19, wherein said medical instrument is selected from the group consisting of an image transmitting device and a surgical instrument.

37. A method of guiding a medical instrument while monitoring an intra-uterine, cervical or tubal procedures, the method comprising the steps of:

(a) inserting an endovaginal ultrasound transducer into a portion of the patient's vagina, said ultrasound transducer being connected to a cervical holder via a connector, said connector being constructed so as to enable counter resisted movement of said ultrasound transducer relative to said cervical holder, said movement being in a direction away from the cervix of the patient;

(b) fixing said ultrasound transducer against a tissue portion of the patient's vagina or cervix via said cervical holder;

(c) inserting a medical instrument through the cervix, aligning said medical instrument with respect to said endovaginal ultrasound transducer and therefore also with respect to an ultrasound beam produced thereby; and (d) monitoring, through the course of the intra-uterine, cervical or tubal procedure, a position of said medical instrument via said ultrasound transducer.

38. The method of claim 37, further comprising providing said connector with:

(i) a cervical holder portion and attaching said cervical holder portion to said cervical holder; and (ii) an ultrasound holder portion and attaching said ultrasound holder portion to said cervical holder portion, said ultrasound holder portion including a body and an ultrasound acceptor being for holding said ultrasound transducer, said acceptor being connected to said body in a manner so as to allow counter resisted movement of said acceptor relative to said body along a longitudinal axis of the apparatus.

39. The method of claim 38, further comprising providing said ultrasound holder portion with a spring element interposed between said acceptor and said body such that said counter resisted movement of said acceptor relative to said body in a direction opposite to the patients cervix is counter resisted by said spring element.

40. The method of claim 38, further comprising providing said ultrasound holder portion with an ultrasound adapter element positioned within said acceptor for firmly holding said ultrasound transducer within said acceptor.

41. The method of claim 38, further comprising providing said ultrasound holder portion of said connector with a construction so as to detach from said cervical holder portion upon an application of a force of a predetermined magnitude to said endovaginal ultrasound transducer along a longitudinal axis thereof.

42. The method of claim 37, further comprising providing said cervical holder with two arms having a securing member, and two holders, said holders being for holding the patient's cervix.

43. The method of claim 42, further comprising providing said cervical holder with an element attached to, or integrally formed with an arm of said two arms, said element being for engaging said cervical holder portion of said connector.

44. The method of claim 37, wherein said step of inserting said medical instrument through the cervix, aligning said medical instrument with respect to said endovaginal ultrasound transducer and therefore also with respect to an ultrasound beam produced thereby is effected by a device including an extension coaxially connected at a distal end of said endovaginal ultrasound transducer.

45. The method of claim 37, wherein said step of inserting said medical instrument through the cervix, aligning said medical instrument with respect to said endovaginal ultrasound transducer and therefore also with respect to an ultrasound beam produced thereby is effected by a device including at least one light beam generator connected either to said connector, to said ultrasound transducer or to said cervical holder, said light beam generator being for generating at least one light beam substantially in a plane defined by said ultrasound beam, said at least one light beam when impinges on said medical instrument serves for facilitating visual alignment of said medical instrument with respect to said endovaginal ultrasound transducer and therefore also with respect to said ultrasound beam.

46. The method of claim 37, wherein said step of inserting said medical instrument through the cervix, aligning said medical instrument with respect to said endovaginal ultrasound transducer and therefore also with respect to an ultrasound beam produced thereby is effected by a device including an imaging device connectable to said endovaginal ultrasound transducer, said imaging device being for generating an image of objects superimposable on a plane defined by said ultrasound beam, thereby facilitating alignment of said medical instrument with respect to said endovaginal ultrasound transducer and therefore also with respect to said ultrasound beam.

47. The method of claim 46, wherein said image is displayed on a screen.

48. The method of claim 46, further comprising providing said imaging device with a camera.

49. The method of claim 48, further comprising providing said camera sensitive to light in the visible range.

50. The method of claim 48, further comprising providing said camera sensitive to infrared light.

51. The method of claim 46, further comprising providing said imaging device with an ultrasound generator.

52. The method of claim 46, further comprising providing said medical instrument with marks along at least a portion thereof, said marks being identifiable by said imaging device so as to be usable for image recognition analysis.

53. The method of claim 37, further comprising providing said device with at least two electromagnetic field generators for generating electromagnetic fields, one of said electromagnetic field generator is connected either to said connector, to said cervical holder or to said ultrasound transducer, whereas the other electromagnetic field generator is connected to said medical instrument, the device further includes at least one electromagnetic field sensor of a predetermined position, such that by analyzing magnetic fields perceived by said at least one electromagnetic sensor, spatial information of the relative locations of said electromagnetic field generators and therefore of said endovaginal ultrasound transducer and said medical instrument is obtainable, thereby facilitating alignment of said medical instrument with respect to said ultrasound beam.

54. The method of claim 37, further comprising providing said medical instrument selected from the group consisting of an image transmitting device and a surgical instrument.

* * * * *